US007319124B2

(12) United States Patent
Weidenhaupt et al.

(10) Patent No.: US 7,319,124 B2
(45) Date of Patent: Jan. 15, 2008

(54) VULCANIZING AGENTS BASED ON ORGANIC SULPHUR-NITROGEN COMPOUNDS FOR UNSATURATED RUBBERS AND MIXTURES OF THESE

(75) Inventors: Hermann-Josef Weidenhaupt, Pulheim (DE); Hartmuth Buding, Titz (DE); Josef Hahn, Köln (DE); Andreas Mihalyi, Erftstadt (DE); Uwe Zettl, Hürth (DE)

(73) Assignee: LANXESS Deutschland GmbH, Leverkusen (DE)

( * ) Notice: Subject to any disclaimer, the term of this patent is extended or adjusted under 35 U.S.C. 154(b) by 288 days.

(21) Appl. No.: 11/094,701

(22) Filed: Mar. 30, 2005
(Under 37 CFR 1.47)

(65) Prior Publication Data
US 2006/0030676 A1    Feb. 9, 2006

(30) Foreign Application Priority Data
Mar. 31, 2004   (DE)   ...................... 10 2004 015 627

(51) Int. Cl.
*C08F 8/34*     (2006.01)
*C08J 3/24*     (2006.01)
*C08C 19/20*    (2006.01)
*C08K 5/43*     (2006.01)

(52) U.S. Cl. .................. 525/351; 525/333.9; 564/100; 568/21

(58) Field of Classification Search ................ 525/351, 525/333.9; 564/100; 568/21
See application file for complete search history.

(56) References Cited

U.S. PATENT DOCUMENTS

| 2,490,518 A | | 12/1949 | Hand | .................. 260/79.5 |
| 3,984,383 A | * | 10/1976 | Akiyama et al. | ........... 525/351 |
| 5,342,900 A | * | 8/1994 | Wolpers et al. | ........... 525/329.3 |

OTHER PUBLICATIONS

Helt W F et al: "Post Vulcanization Stabilization for NR" Rubber World, Lippincott & Peto, Akron, OH, US. Bd. 204, Nr. 5, Jan. 1991, Seiten 18-24, XP000610653 ISSN: 0035-9572 Seite 18-Seite 19; Tabellen 2, 5, 7, 9, Seite 21 Seite 23-24.
Patent Abstracts of Japan; Bd. 1998, Nr. 02, Jan. 30, 1998 & JP 09 278942 A (Sumitomo Rubber Ind Ltd), Oct. 28, 1997 Zusammenfassung.
Patent Abstracts of Japan; Bd. 2000, Nr 19, Jun. 5, 2001 & JP 2001 031797 A (Yokohama Rubber Co Ltd: The), Feb. 6, 2001 Zusammenfassung.
W. Hofmann, Kaurschuk-Technologie [Rubber Technology], Genter Verlag, Stuttgart, 1980, p. 64 and 254-255.
R.N. Datta and W.F. Helt, Rubber World, Aug. 1997, p. 24, seq. "Optimizing tire compound Reversion resistance without sacrificing performance characteristics".

* cited by examiner

*Primary Examiner*—Roberto Rabago
(74) *Attorney, Agent, or Firm*—Nicanor A. Kohncke

(57) ABSTRACT

The invention relates to novel organic sulphur-nitrogen compounds, their preparation, and use as vulcanizing agents for unsaturated rubbers and mixtures of these.

5 Claims, No Drawings

VULCANIZING AGENTS BASED ON ORGANIC SULPHUR-NITROGEN COMPOUNDS FOR UNSATURATED RUBBERS AND MIXTURES OF THESE

CROSS REFERENCE TO RELATED PATENT APPLICATIONS

The present patent application claims the right of priority under 35 U.S.C. §119 (a)-(d) of German Patent Application No.'s DE 102004015627.131 March 2004.

FIELD OF THE INVENTION

The invention relates to novel organic sulphur-nitrogen compounds, their preparation, and use as vulcanizing agents for unsaturated rubbers and mixtures of these.

Sulphur continues to be the most commonly used vulcanizing agent for unsaturated rubbers, e.g. natural rubber (NR), isoprene rubber (IR), butadiene rubber (BR) and styrene-butadiene rubber (SBR). From about 0.25 to 5.0 parts by weight of sulphur, based on 100 parts by weight of unvulcanized rubber, are used in the production of soft rubber. The amount of sulphur effectively used depends on the selected amount of vulcanization accelerator, and this is ultimately determined via the vulcanizates properties desired.

Vulcanization systems very frequently used are the conventional vulcanization system and the semi-efficient vulcanization system. The conventional vulcanization system has high sulphur content and low content of vulcanization accelerator, whereas the semi-efficient vulcanization system has a moderate proportion of sulphur and of vulcanization accelerator. The typical proportions are known to the person skilled in the art. By way of example, they are described in W. Hofmann, Kautschuk-Technologie [Rubber Technology], Genter Verlag, Stuttgart, 1980, p. 64 and 254-255. Conventional vulcanization systems give vulcanizates with good resistance to dynamic load, but these are very susceptible to ageing and reversion. Semi-efficient vulcanization systems usually give vulcanizates which have less resistance to dynamic load but are somewhat more resistant to ageing and reversion.

Reversion is a network-bridging-rearrangement process which takes place on heating in the absence of oxygen, causing impairment of service properties of the vulcanizate and therefore being undesirable (anaerobic ageing). Reversion inevitably takes place in one instance during the vulcanization of very thick and voluminous components, e.g. truck tyres and fenders. Physical explanation of this is simple: when the inner parts of the rubber mixture have been vulcanized to exactly the right extent via the heat flux introduced by way of the hot vulcanization mould, those parts of the rubber mixture that are immediately adjacent to the hot vulcanization mould have naturally by this stage been over-vulcanized. Secondly, heat build-up occurs in the rubber component during its use when there is prolonged, intensive dynamic load due to hysteresis deficiencies (cf. tyre flexing energy), the result of this being vulcanizate reversion. The extent of reversion can even be sufficient to cause breakdown, and therefore failure, of the vulcanizate.

In recent years, some specialized reversion stabilizers have been disclosed, and these either minimize reversion via incorporation of network bridges which are thermally stable and practically incapable of reversion (cf. EP-A 530 590), or replace the fractured conventional sites in the network by other more stable sites after reversion has occurred (cf. R. N. Datta and W. F. Helt, Rubber World, August 1997, p. 24 seq).

Examples of specialized reversion stabilizers available commercially are the disodium salt of hexamethylene 1,6-dithiosulphate dihydrate and 1,3-bis(citraconimidomethyl)benzene.

A general disadvantage of these commercially available specialized reversion stabilizers is their relatively high price, partly the result of starting materials available only in limited quantities, and also of the difficult and complicated preparation of these products, therefore preventing any broad use in the rubber-processing industry, which is subject to constant pressure for cost reduction, and especially in the tyre industry. One specific disadvantage of the disodium salt of hexamethylene 1,6-dithiosulphate dihydrate is its inconvenient supply form. Because it has the character of a salt, it has to be very finely ground to permit good incorporation by mixing, but the result of this is that the powder has to be oil-coated for reasons of health and safety at work, to suppress dusting.

One specific disadvantage of 1,3-bis(citraconimidomethyl)benzene is that within the vulcanizate it can become active only when reversion has already begun in the sulphur-crosslinked unsaturated rubber, and when, therefore, conjugated olefins have formed, which themselves can undergo a post-crosslinking reaction with the citraconic derivative (via a Diels-Alder reaction) to give a new network, but a network of a different type.

A disadvantage of the vulcanizing agents of EP 530 590 is that their molecular weight is high when compared with the actual species active in crosslinking.

Polymeric alkylene-sulphur- or arylene-sulphur-nitrogen compounds have been known for a long time. For example, polyphenylene sulphide (PPS) is a product used as a thermoplastic. No use as a vulcanizing agent for rubber has been disclosed. Some experiments confirm, as in Example 9, that PPS does not crosslink a black natural rubber mixture. Polymeric alkylene-sulphur compounds are also described. Depending on the sulphur chain length, crosslinking of unsaturated rubbers can take place. However, the high proportion of crosslinking agent suggests incorporation of two or more alkylene-sulphur units per network site, and therefore unsatisfactory network site yield.

Large-scale production of vulcanizates from unsaturated rubbers usually uses only sulphur and accelerators as vulcanizing agents, i.e. uses no agents which prevent or reduce reversion. However, rubber vulcanizates produced conventionally, using conventional and semi-efficient vulcanization systems, have unsatisfactory properties. There is therefore a need for a vulcanizing agent for unsaturated rubbers which is largely based on components which are readily available in large quantities at low cost, and which is technically simple to prepare, and which, in a vulcanization system, can partially or completely replace extrusion-susceptible crystalline sulphur, and which gives vulcanizates with improved resistance to reversion, in particular after overheating.

Surprisingly, the object is achieved via vulcanization of an unsaturated rubber mixture with specific novel organic sulphur-nitrogen compounds.

The invention therefore provides organic sulphur-nitrogen compounds of the formula (I)

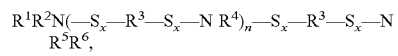

where
- $R^1$, $R^2$, $R^5$ and $R^6$ are identical or different and are hydrogen, methyl, ethyl, n-butyl, isobutyl, tert-butyl, hexyl, cyclohexyl, octyl, phenyl or benzyl,
- $R^4$ is methyl, ethyl, n-butyl, isobutyl, tert-butyl, hexyl, cyclohexyl, octyl, phenyl or benzyl,
- n is a whole number from 1 to 50, preferably from 1 to 10 with the proviso that n=0 if $R^1$, $R^2$, $R^5$ or $R^6$ is not hydrogen,
- $R^3$ is phenylene, methylene, ethylene, butylene or hexanediyl and
- x is a whole number from 2 to 6.

$R^1$, $R^2$, $R^5$ and $R^6$ are preferably methyl, ethyl, tert-butyl, benzyl, cyclohexyl, $R^4$ is preferably methyl, ethyl, tert-butyl, benzyl, cyclohexyl, $R^3$ is preferably phenylene or hexanediyl and x is preferably whole numbers from 2 to 4.

The invention also provides the preparation of the organic sulphur-nitrogen compounds of the above formula and use of these as vulcanizing agents for unsaturated rubbers.

The inventive organic sulphur-nitrogen compounds of the above formula are obtained via reaction of the appropriate amine component with appropriate bis(dichloropolysulphonyl)arylenes or -alkylenes, e.g. 1,4-bis(chlorodisulphanyl) benzene or 1,6-bis(chlorotrisulphanyl)hexane in inert solvents at room temperature. The precipitated salt is filtered off. The organic phase is washed with water until free from salt and dried, and then the solvent is removed by distillation. The novel compounds can be used in the form of bottom product without further work-up for the vulcanization process. The sulphur-nitrogen compounds can also be obtained (see Example 8) via degradation of the appropriate poly(polythio)alkanes.

The sulphur-chlorine compounds to be used can, of course, be used directly from their synthesis without further prior purification. They then also comprise oligomeric fractions. The oligomeric fraction may be up to 80% by weight, based on starting compound, preferably up to 50% by weight.

If secondary amines are used, monomeric organic amine crosslinking agents are necessarily always obtained. If primary amines are used, oligomeric organic structures can also be obtained, depending on the amine excess used. If the amine excess is very small these should predominate. Examples of primary amines which may be used are methylamine, ethylamine, propylamine, isobutylamine, n-butylamine, tert-butylamine, hexylamine, cyclohexylamine, benzylamine, phenylamine or octylamine. Examples of secondary amines which may be used are dimethylamine, diethylamine, dipropylamine, di-tert-butylamine, diisobutylamine, di-n-butylamine, dicyclohexylamine, dibenzylamine, diphenylamine, dioctylamines, methylphenylamine, ethylphenylamine or dihexylamine.

1,4-bis(chlorodisulphanyl)benzene can be obtained in good yields, by way of example, via reaction of benzene with dichlorodisulphane, using Lewis acids as catalysts. Examples of suitable catalysts are ®KSF montmorillonite from ACROS (BET surface area from 20 to 40 m$^2$/g), ®K10 montmorillonite (BET surface area from 220 to 270 m$^2$/g) or Vulkasil® S/aluminium trichloride (Vulkasil S being a precipitated silica from Bayer Material Science AG with a BET surface area of 175 m$^2$/g).

The inventive organic sulphur-nitrogen compounds of the above formula may, by way of example, be used as vulcanizing agents for unsaturated rubber mixtures for production of rubber mouldings, e.g. hoses, gaskets, engine mountings and fenders, and particularly for production of tyre components, e.g. treads, wire caps, sidewall sections and bead sections, shoulder blocks, belt coverings, cap plies and sidewalls.

The inventive rubber mixtures are prepared in a manner known per se via conventional mixing of the unsaturated rubber components with the known additives, such as carbon black, silica, plasticizer, antioxidant, zinc oxide, stearic acid, resin, processing aid, and also the vulcanization system composed of the inventive novel organic sulphur-nitrogen compounds and, if appropriate, also elemental sulphur.

The inventive organic sulphur-nitrogen compounds may either be used during preparation of the parent mixture, providing meticulous exclusion of any excipient vulcanization, or may preferably be used during preparation of the finished mixture together with the vulcanization accelerators and sulphur, if desired.

Examples of unsaturated rubbers for the purposes of the invention are nature rubber (NR), isoprene rubber (IR), butadiene rubber (BR) and styrene-butadiene rubber (SBR), which may have been prepared by the emulsion process or else by the solution process, nitrile rubber (NBR), partially hydrogenated nitrile rubber (HNBR) and ethylene-propylene-diene rubber (EPDM). Equally good results are obtained with blends of these rubbers.

There is no restriction on the use of carbon blacks. It is preferable to use the carbon blacks typically used in the rubber-processing industry, for example active or semiactive carbon blacks.

There is likewise no restriction on the use of silicas. Preference is given to fine-particle silicas prepared via precipitation from solutions of silicates or via flame hydrolysis of silicon halides. The specific surface area of preferred silicas is from 20 to 400 m$^2$/g (BET surface area) and their primary particle size is from 10 to 400 nm.

The amounts used of the inventive sulphur-nitrogen compounds, based on 100 parts by weight of rubber, are from about 0.2 to 10 parts by weight, preferably from 0.5 to 6.0 parts by weight. If sulphur is also to be used, the sulphur used may be that usually used in the rubber-processing industry, or else insoluble sulphur. The preferred amount of sulphur is from about 0.05 to 2.5 parts by weight, preferably from 0.1 to 1.5 parts by weight, based on 100 parts by weight of rubber.

Instead of sulphur, the known sulphur donors may, of course, also be used, an example being caprolactam disulphide, or else mixtures with sulphur. The advantageous amount of sulphur donor for the intended use can easily be determined via preliminary experiments.

There is no restriction on the vulcanization accelerators which may be used, which may be of a very wide variety of types. It is preferable to use mecaptobenzothiazole (MBT), dibenzothiazyl disulphide (MBTS), sulphenamides based on MBT, e.g. benzothiazyl-2-cyclohexylsulphen-amide (CBS), benzothiazyl-2-dicyclohexylsulphenamide (DCBS), benzothiazyl-2-tert-butylsulphenamide (TBBS) and benzothiazyl-2-sulphene morpholide (MBS). The amounts used of vulcanization accelerators are from 0.5 to 4.0 parts by weight, preferably from about 1.0 to 3.5 parts by weight, based on 100 parts by weight of rubber used. However, it is also possible to use mixtures of vulcanization accelerators, and the ideal composition of these, in relation to type and amounts, can readily be determined experimentally.

The inventive rubber mixtures are vulcanized in a known manner at temperatures from about 120 to 220° C., preferably from 140 to 180° C.

The present invention has been described with reference to specific details of particular embodiments thereof and examples, infra. It is not intended that such details be regarded as limitations upon the scope of the invention except insofar as and to the extent that they are included in the accompanying claims.

It should also be understood the meaning of words spelled using British English and American English shall have the identical meanings. (E.g. moulding/molding; tyre/tire).

EXAMPLES

Preparation of Inventive Organic Sulphur Compounds of the Formula (I)

Example 1

Synthesis of 1,4-bis(diethylaminodisulphanyl)benzene 25.0 ml (190 mmol) of diethylamine are used as initial charge in 150 ml of 1,2-dichloroethane in an inertized three-necked flask with dropping funnel, reflux condenser with hose coupling at its upper end, a tap with hose coupling and a Teflon stirrer bar, in a countercurrent of argon. 10.6 g (38.6 mmol) of 1,4-bis(chlorodisulphanyl)benzene in 50 ml of 1,2-dichloroethane are then slowly added dropwise, with stirring. The reaction mixture is stirred at room temperature for 4 hours. The resultant salt is filtered off, and the organic phase is washed three times with water and dried over sodium sulphate. After removal of the solvent on a rotary evaporator and drying in the vacuum generated by a rotary-vane pump, 1,4-bis(diethylaminodisulphanyl)benzene precipitates in the form of a yellow oil. The crude yield is 11.9 g (89%). Elemental analysis was carried out on the crude product.

| C calc.: 48.23 | H calc.: 6.94 | N calc.: 8.04 | S calc.: 36.79 |
|---|---|---|---|
| C found: 44.88 | H found: 5.62 | N found: 6.33 | S found: 34.17 |

Example 2

Synthesis of 1,4-bis(t-butylaminodisulphanyl)benzene 100 ml (941 mmol) of tert-butyl are used as initial charge in 1,2-dichloroethane in an inertized three-necked flask with dropping funnel, reflux condenser with hose coupling at its upper end, a tap with hose coupling and a Teflon stirrer bar, in a countercurrent of argon. 10.6 ml (38.6 mmol) of 1,4-bis(chlorodisulphanyl)benzene in 50 ml of 1,2-dichloroethane are then slowly added dropwise, with stirring. The reaction mixture is stirred at room temperature for 4 hours. The resultant salt is filtered off, and the organic phase is washed three times with water and dried over sodium sulphate. After removal of the solvent on a rotary evaporator and drying in the vacuum generated by a rotary-vane pump, 1,4-bis(tert-butylaminodisulphanyl)benzene precipitates in the form of a yellow oil. The crude yield is 11.9 g (88%). Elemental analysis was carried out on the crude product.

| C calc.: 48.23 | H calc.: 6.94 | N calc.: 8.04 | S calc.: 36.79 |
|---|---|---|---|
| C found: 40.74 | H found: 4.88 | N found: 5.74 | S found: 44.10 |

Example 3

Synthesis of α-tert-butylamino-ω-hydropoly[1-disulphanyl-4-(tert-butylaminodisulphanyl)phenylene]

11.7 g (42.4 mmol) of 1,4-bis(chlorodisulphanyl)benzene are used as initial charge in 1,2-dichloroethane in an inertized three-necked flask with dropping funnel, reflux condenser with hose coupling at its upper end, a tap with hose coupling and a Teflon stirrer bar, in a countercurrent of argon. 13.4 g (125 mmol) of tert-butylamine are then added dropwise, with stirring. The reaction mixture is stirred at room temperature for 4 hours. The resultant salt is filtered off, and the organic phase is washed three times with water and dried over sodium sulphate. After removal of the solvent on a rotary evaporator and drying in the vacuum generated by a rotary-vane pump, α-tert-butylamino-ω-hydropoly[1-disulphanyl-4-(tert-butylaminodisulphanyl)phenylene] precipitates in the form of a yellow resin. The crude yield is 12.7 g (99%). Elemental analysis was carried out on the crude product.

| C calc.: 43.60 | H calc.: 4.76 | N calc.: 5.08 | S calc.: 46.56 |
|---|---|---|---|
| C found: 36.88 | H found: 4.46 | N found: 5.32 | S found: 36.61 |

Example 4

Synthesis of 1,6-bis(diethylaminotrisulphanyl)hexane 20.0 ml (152 mmol) of diethylamine are used as initial charge in 1,2-dichloroethane in an inertized three-necked flask with dropping funnel, reflux condenser with hose coupling at its upper end, a tap with hose coupling and a Teflon stirrer bar, in a countercurrent of argon. 10.4 g (29.7 mmol) of 1,6-bis(chlorotrisulphanyl)hexane in 50 ml of 1,2-dichloroethane are then slowly added dropwise, with stirring. The reaction mixture is stirred at room temperature for 4 hours. The resultant salt is filtered off, and the organic phase is washed three times with water and dried over sodium sulphate. After removal of the solvent on a rotary evaporator and drying in the vacuum generated by a rotary-vane pump, 1,6-bis(diethylaminotrisulphanyl)hexane precipitates in the form of a yellow oil. The crude yield is 5.32 g (82%). Elemental analysis was carried out on the crude product.

| C calc.: 39.96 | H calc.: 7.67 | N calc.: 6.66 | S calc.: 45.72 |
|---|---|---|---|
| C found: 39.33 | H found: 7.63 | N found: 5.75 | S found: 45.97 |

Example 5

Synthesis of 1,6-bis(tert-butylaminotrisulphanyl)hexane 70.0 ml (736 mmol) of tert-butylamine are used as initial charge in 1,2-dichloroethane in an inertized three-necked flask with dropping funnel, reflux condenser with hose coupling at its upper end, a tap with hose coupling and a Teflon stirrer bar, in a countercurrent of argon. 10.2 g (29.3 mmol) of 1,6-bis(chlorotrisulphanyl)hexane in 50 ml of 1,2-dichloroethane are then added dropwise, with stirring. The reaction mixture is stirred at room temperature for 4 hours. The resultant salt is filtered off, and the organic phase is washed three times with water and dried over sodium sulphate. After removal of the solvent on a rotary evaporator and drying in the vacuum generated by a rotary-vane pump, 1,6-bis(tert-butylaminotrisulphanyl)hexane precipitates in the form of a yellow oil. The crude yield is 11.9 g (97%). Elemental analysis was carried out on the crude product.

| | | | |
|---|---|---|---|
| C calc.: 39.96 | H calc.: 7.67 | N calc.: 6.66 | S calc.: 45.72 |
| C found: 38.82 | H found: 7.46 | N found: 5.15 | S found: 45.87 |

Example 6

Synthesis of α-tert-butylamino-ω-hydropoly[1-trisulphanyl-4-(tert-butylaminotrisulphanyl)hexanediyl]

11.2 g (32.2 mmol) of 1,6-bis(chlorotrisulphanyl)hexane are used as initial charge in 150 ml of 1,2-dichloroethane in an inertized three-necked flask with dropping funnel, reflux condenser with hose coupling at its upper end, a tap with hose coupling and a Teflon stirrer bar, in a countercurrent of argon. 10.0 ml (94.7 mmol) of tert-butylamine in 50 ml of 1,2-dichloroethane are then added dropwise, with stirring. The reaction mixture is stirred at room temperature for 4 hours. The resultant salt is filtered off, and the organic phase is washed three times with water and dried over sodium sulphate. After removal of the solvent on a rotary evaporator and drying in the vacuum generated by a rotary-vane pump, α-tert-butylamino-ω-hydropoly[1-trisulphanyl-4-(tert-butylminotri-sulphanyl)hexanediyl] precipitates in the form of a yellow resin. The yield is 64.4 g (99%). Elemental analysis was carried out on the crude product.

| | | | |
|---|---|---|---|
| C calc.: 34.55 | H calc.: 6.09 | N calc.: 4.03 | S calc.: 55.34 |
| C found: 34.70 | H found: 6.20 | N found: 3.34 | S found: 53.63 |

Example 7

Synthesis of α-cyclohexylamino-ω-hydrooligo[1-disulphanyl-4-(disulphanylcyclohexylamino)phenylene]

375.0 ml (3.4 mol) of cyclohexylamine are used as initial charge in 100 ml of tetrachloromethane in an inertized three-necked flask with dropping funnel, reflux condenser with hose coupling at its upper end, a tap with hose coupling and a Teflon stirrer bar, in a countercurrent of argon. 51.3 g (190 mmol) of 1,4-bis(chlorodisulphanyl)benzene in 50 ml of tetrachloromethane are then slowly added dropwise, with stirring. The reaction mixture is stirred at room temperature for 36 hours. The resultant salt is filtered off, and the organic phase is washed three times with water and dried over sodium sulphate. After removal of the solvent on a rotary evaporator and drying in the vacuum generated by a rotary-vane pump, α-cyclohexylamino-ω-hydrooligo[1-disulphanyl-4-(disulphanylcyclohexylamino)phenylene] precipitates in the form of a viscose, sticky brown oil. The crude yield is 65.8 g (86%).

Example 8

Synthesis of bis(diethylaminooligosulphanyl)hexane via polymer degradation 100 ml (760 mmol) of diethylamine and 2.73 g (12.9 mmol) of poly(1,6-tetrathiohexanediyl) in 200 ml of chloroform are added to a 500 ml round-bottomed flask with reflux condenser with calcium chloride drying tube at its upper end. The reaction mixture is then maintained at reflux for 5 days, with stirring. The resultant salt is filtered off and the organic phase is washed three times with water and dried over sodium sulphate. After removal of the solvent on a rotary evaporator and drying in the vacuum generated by a rotary-vane pump, 3.52 g (93%) of 1,6-bis(diethylaminooligosulphanyl)hexane precipitates in the form of a dark red oil.

Explanations of Vulcanizate Tests

The following test methods and test apparatus were used: Rheometer: ASTM D 2084, Monsanto MDR 2000E. Tensile test: DIN 53405, S2 specimen. Hardness: DIN 53505. Rebound resilience: DIN 53512. Tear propagation resistance: DIN 53504. Abrasion DIN 53516. Viscoelectric properties: DIN 53513/ISO 4664, Roelig test 10 Hz. Dynamic properties: DIN 53533.

Example 9

The organic vulcanizing agents were tested in a carbon-black-filled natural rubber mixture (100 parts of NR, 5 parts of RS ZnO, 1 part of stearic acid, 50 parts of N375 carbon black, 6 parts of 6PPD, 1 part of TMQ, 1 part of ozone-stabilizer wax, 3 parts of aromatic plasticizer). The preparation process used a Werner & Pfleiderer GK 1.5E internal mixer. Sulphur, accelerator (CBS) and vulcanizing agent were incorporated subsequently on a roll mill. The amounts stated are parts by weight per 100 parts by weight of rubber.

TABLE 1

| | Proportion of crosslinking agent |
|---|---|
| Comparison 1: | 1 part of sulphur |
| Polyphenylene sulphide: | 3 parts polyphenylene sulphide |
| Example 1: | 1.26 parts of compound according to Example 1, 0.57 part of sulphur |
| Example 2: | 1.57 parts of compound according to Example 2, 0.49 part of sulphur |
| Example 3: | 1.26 parts of compound according to Example 3, 0.57 part of sulphur |
| Example 4: | 1.86 parts of compound according to Example 4, 0.36 part of sulphur |
| Example 5: | 1.86 parts of compound according to Example 5, 0.36 part of sulphur |
| Example 6: | 1.59 parts of compound according to Example 6, 0.36 part of sulphur |

3.4 parts of CBS were added as accelerator to each mixture.

TABLE 2

Determination of reversion in a rheometer

|  | Torque relative to Comparison 1 | Reversion relative to Comparison 1 |
| --- | --- | --- |
| Comparison 1 | 100% | 100% |
| Polyphenylene sulphide | 12% | — |
| Example 1 | 97% | 75% |
| Example 2 | 99% | 47% |
| Example 3 | 99% | 61% |
| Example 4 | 107% | 8% |
| Example 5 | 111% | 3% |
| Example 6 | 106% | 5% |

Reversion in % was determined as follows from the rheometer data (160° C., 60 min):

(S'max−S'end)×1/S'max×100 (%), and calculated relative to comparison 1.

Firstly, Table 2 shows that the mixtures according to the invention have markedly higher resistance to reversion (the smaller the reversion value, the higher the resistance to reversion) than comparative mixture 1. Secondly, polyphenylene sulphide has practically no crosslinking activity, therefore making it pointless to calculate the resistance to reversion.

Example 10

Test mixtures according to Table 3 were prepared with the aid of a Werner & Pfleiderer GK 1,5E internal mixer, using a rotor rotation rate of 40 rpm and a chamber and rotor temperature of 50° C. (ram pressure 8 bar, fill level 65%).

Accelerator, sulphur and the novel sulphur compounds according to Example 7 were admixed on a roll mill. The quantitative data represent parts by weight per 100 parts by weight of rubber.

TABLE 3

Test mixing specification

|  | Comparison | Invention |
| --- | --- | --- |
| Mixture number | 1 | 2 |
| NR (TSR 5, Defo 700) | 100 | 100 |
| RS zinc oxide | 5 | 5 |
| Stearic acid | 1 | 1 |
| N375 carbon black | 50 | 50 |
| 6PPD | 2 | 2 |
| TMQ | 1 | 1 |
| Ozone-stabilizer wax | 1 | 1 |
| Arom. plasticizer | 3 | 3 |
| Sulphur | 1.5 | 0.5 |
| CBS | 1.5 | 1.5 |
| Sulphur compound according to Example 7 (invention) | 0 | 3 |

TABLE 4

Rheometer data

|  | Comparison | Invention |
| --- | --- | --- |
| Mixture number 150° C./60 min | 1 | 2 |
| t01 (min) | 2.75 | 1.1 |
| t90 (min) | 5.67 | 4.17 |
| S' max (dNm) | 22.19 | 19.62 |

TABLE 4-continued

Rheometer data

|  | Comparison | Invention |
| --- | --- | --- |
| S' end (dNm) | 19.91 | 19.33 |
| Reversion (%) | 10.3 | 1.5 |

Reversion in % was determined as follows from the rheometer data: (S'max−S'end)×1/S'max×100 (%)

Table 4 shows firstly that the mixtures according to the invention have markedly higher resistance to reversion (the smaller the reversion value, the higher the resistance to reversion) than comparative mixture 1.

TABLE 5

Properties of test vulcanizates after optimized heating

|  | Comparison | Invention |
| --- | --- | --- |
| Mixture number | 1 | 2 |
| Vulcanization: 150° C./11 min |  |  |
| Strength (MPa) | 32 | 32 |
| Tensile strain at break (%) | 555 | 579 |
| 100 modulus (MPa) | 2.6 | 2.5 |
| 300 modulus (MPa) | 13.8 | 13.0 |
| Tear propagation resistance (N) | 64 | 61 |
| Hardness at 23° C. (Shore A) | 65 | 65 |
| Elasticity at 23° C. (%) | 44 | 44 |
| Abrasion (mm$^3$) | 109 | 122 |
| Roelig 0° C. |  |  |
| tan delta | 0.232 | 0.215 |
| E' (MPa) | 11.036 | 11.954 |
| E" (MPa) | 2.562 | 2.570 |
| Roelig 60° C. |  |  |
| tan delta | 0.125 | 0.137 |
| E' (MPa) | 6.675 | 7.015 |
| E" (MPa) | 0.833 | 0.959 |

Table 5 shows that after optimized heating the properties of the vulcanizates according to the invention are comparable with those of the comparative vulcanizate.

TABLE 6

Properties of test vulcanizates after overheating

|  | Comparison | Invention |
| --- | --- | --- |
| Mixture number | 1 | 2 |
| Vulcanization: 160° C./120 min |  |  |
| Strength (MPa) | 25.2 | 26.8 |
| Tensile strain at break (%) | 547 | 518 |
| 100 modulus (MPa) | 2.0 | 2.4 |
| 300 modulus (MPa) | 10.5 | 13.0 |
| Tear propagation resistance (N) | 34 | 45 |
| Hardness at 23° C. (Shore A) | 63 | 62 |
| Elasticity at 23° C. (%) | 45 | 41 |
| Abrasion (mm$^3$) | 228 | 158 |
| Roelig 0° C. |  |  |
| tan delta | 0.249 | 0.230 |
| E' (MPa) | 10.194 | 12.500 |
| E" (MPa) | 2.538 | 2.876 |
| Roelig 60° C. |  |  |
| tan delta | 0.150 | 0.149 |
| E' (MPa) | 5.587 | 6.683 |
| E" (MPa) | 0.835 | 0.995 |

Table 6 shows that, after overheating, the vulcanizates according to the invention have better retention of modulus, strength, tear propagation resistance and abrasion than does the comparative vulcanizate.

What is claimed is:

1. Organic sulphur-nitrogen compounds of the formula

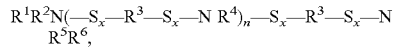

where
- $R^1$, $R^2$, $R^5$ and $R^6$ are identical or different and are hydrogen, methyl, ethyl, n-butyl, isobutyl, tert-butyl, hexyl, cyclohexyl, octyl, phenyl or benzyl,
- $R^4$ is methyl, ethyl, n-butyl, isobutyl, tert-butyl, hexyl, cyclohexyl, octyl, phenyl or benzyl,
- n is a whole number from 1 to 50, with the proviso that n=0 if $R^1$, $R^2$, $R^5$ or $R^6$ is not hydrogen,
- $R^3$ is phenylene, methylene, ethylene, butylene or hexylene and
- x is a whole number from 2 to 6.

2. A process for the preparation of the organic sulphur-nitrogen compounds according to claim 1, comprising reacting an amine with bis(dichloropolysulphanyl)arylenes or -alkylenes in one or more inert solvents.

3. A process for preparing unsaturated rubber-vulcanizates, comprising vulcanizing unsaturated rubber in the presence of the organic sulphur-nitrogen compounds according to claim 1.

4. A process for producing rubber moldings, comprising forming the rubber moldings in the presence of the sulphur-nitrogen compounds according to claim 1.

5. A process for producing tire components, comprising forming the tire components in the presence of the sulphur-nitrogen compounds according to claim 1.

* * * * *